US008283299B2

(12) United States Patent
Allef et al.

(10) Patent No.: US 8,283,299 B2
(45) Date of Patent: Oct. 9, 2012

(54) SKIN AND HAND CLEANING COMPOSITIONS WITH HYDROPHILIC EMOLLIENTS

(75) Inventors: Petra Allef, Krefeld (DE); Volker Klotzbach, Wachtendonk (GB); Marcel Veeger, Goch (DE)

(73) Assignee: Evonik Stockhausen GmbH, Krefeld (DE)

( * ) Notice: Subject to any disclaimer, the term of this patent is extended or adjusted under 35 U.S.C. 154(b) by 0 days.

(21) Appl. No.: 12/595,531

(22) PCT Filed: Apr. 22, 2008

(86) PCT No.: PCT/EP2008/054834
§ 371 (c)(1),
(2), (4) Date: Oct. 12, 2009

(87) PCT Pub. No.: WO2008/138708
PCT Pub. Date: Nov. 20, 2008

(65) Prior Publication Data
US 2010/0210499 A1 Aug. 19, 2010

(30) Foreign Application Priority Data

May 11, 2007 (DE) .......................... 10 2007 022 693

(51) Int. Cl.
*A61K 7/50* (2006.01)
(52) U.S. Cl. ........ 510/130; 510/136; 510/156; 510/424; 510/505
(58) Field of Classification Search ........................ None
See application file for complete search history.

(56) References Cited

U.S. PATENT DOCUMENTS

| 5,658,577 | A | 8/1997 | Fowler et al. |
| 5,888,951 | A | 3/1999 | Gagnebien et al. |
| 6,376,438 | B1 | 4/2002 | Rosenberger et al. |
| 6,432,430 | B1 | 8/2002 | Fitzjarrell |
| 6,471,983 | B1 | 10/2002 | Veeger et al. |

(Continued)

FOREIGN PATENT DOCUMENTS

DE          40 09 534          9/1991
(Continued)

OTHER PUBLICATIONS

U.S. Appl. No. 12/674,831, filed Feb. 23, 2010, Wenk, et al.

(Continued)

*Primary Examiner* — Necholus Ogden, Jr.
(74) *Attorney, Agent, or Firm* — Oblon, Spivak, McClelland, Maier & Neustadt, L.L.P.

(57) ABSTRACT

The invention relates to skin cleansers/hand cleaners, particularly coarse hand cleaners, containing at least 0.1 wt. % of at least one hydrophilic emollient having an HLB value of $\geq 10$. Said skin cleansers/hand cleaners especially contain, relative to the entire composition of the cleanser/cleaner, a.) at least 0.1 wt. % of at least one hydrophilic emollient, preferably a polyol ester, b.) 2 to 40 wt. % of at least one surfactant selected from among the group comprising fatty alcohol ethoxylates, fatty alcohol ether sulfates, and salts of sulfated and/or sulfonated fatty acids, c.) 30 to 90 wt. % of water, d.) 0 to 30 wt. % of one or more cleaning promoters selected from among the group comprising polyols, polyether, polyphosphates, and phosphates, e.) 0 to 30 wt. % of one or more abrasive agents, f.) 0 to 1.0 wt. % of propoxylated fatty alcohols, g.) one or more optional viscosity-forming agents, h.) other optional cosmetic auxiliary agents, additives, and/or active substances, the total of components a.) to h.) amounting to 100 wt. %.

17 Claims, 11 Drawing Sheets

U.S. PATENT DOCUMENTS

| | | |
|---|---|---|
| 6,489,275 B1 | 12/2002 | Veeger et al. |
| 7,163,916 B2 | 1/2007 | Allef et al. |
| 7,241,452 B2 | 7/2007 | Veeger et al. |
| 7,297,675 B2 | 11/2007 | Allef et al. |
| 2003/0049212 A1* | 3/2003 | Robinson et al. ............ 424/59 |
| 2004/0170592 A1 | 9/2004 | Veeger et al. |
| 2005/0031580 A1 | 2/2005 | Allef et al. |
| 2006/0165627 A1 | 7/2006 | Allef et al. |
| 2006/0182690 A1 | 8/2006 | Veeger et al. |
| 2006/0198859 A1 | 9/2006 | Allef et al. |
| 2006/0204468 A1 | 9/2006 | Allef et al. |
| 2007/0041927 A1 | 2/2007 | Blaeser et al. |
| 2007/0072780 A1 | 3/2007 | Reddy et al. |
| 2007/0092470 A1 | 4/2007 | Allef et al. |
| 2008/0145320 A1 | 6/2008 | Wenk et al. |
| 2008/0305056 A1 | 12/2008 | Jenni et al. |
| 2009/0054521 A1 | 2/2009 | Herrwerth et al. |
| 2010/0069505 A1 | 3/2010 | Veeger et al. |

FOREIGN PATENT DOCUMENTS

| | | |
|---|---|---|
| DE | 199 16 036 | 10/2000 |
| DE | 10 2004 025287 | 12/2005 |
| EP | 1 152 051 | 11/2001 |

OTHER PUBLICATIONS

U.S. Appl. No. 12/863,868, filed Jul. 21, 2010, Allef, et al.
U.S. Appl. No. 12/933,835, filed Sep. 21, 2010, Allef, et al.
U.S. Appl. No. 12/514,326, filed May 11, 2009, Veeger, et al.
U.S. Appl. No. 12/446,569, filed Apr. 21, 2009, Veeger, et al.
U.S. Appl. No. 13/379,064, filed Dec. 22, 2011, Thoerner, et al.
U.S. Appl. No. 13/380,064, filed Dec. 22, 2011, Allef, et al.

\* cited by examiner

Fig. 1A

| Ingredients according to INCI nomenclature | A | B | C | D | E | F | G | H | I |
|---|---|---|---|---|---|---|---|---|---|
| AQUA (WATER) | 57.3 | 60.5 | 60.2 | 57.0 | 58.9 | 48.7 | 65.8 | 71.4 | 76.0 |
| JUGLANS REGIA SHELL POWDER | 15.0 | 15.0 | 15.0 | 15.0 | 15.0 | 15.0 | 12.0 | 6.0 | 6.0 |
| QUARTZ SAND | | | | | | | | | |
| Sodium carbonate | | | | | | | | | |
| Rapeseed oil | | | | | | | | | |
| Sodium lauryl sulphate | | | | | | | | | |
| LAURETH-6 | 9.0 | 6.0 | 6.0 | 9.9 | | | 6.0 | 6.0 | 6.0 |
| LAURETH-5 | | | | | | 9.0 | | | |
| POLOXAMER 407 (EO/PO block polymer – Pluronic) | | | | | 6.0 | | | | |
| ALKYL POLYGLUCOSIDE | | | | | | | | | |
| SODIUM LAURETH SULPHATE | 3.1 | 3.1 | 3.1 | 3.1 | 5.0 | 3.0 | 3.3 | 3.3 | |
| SULPHATED CASTOR OIL | 2.8 | 2.8 | 2.8 | 2.8 | 2.5 | 2.5 | 2.8 | 2.8 | |
| DISODIUM LAURETH SULPHOSUCCINATE | 3.0 | 2.1 | 2.1 | 2.4 | 1.0 | 3.0 | 1.8 | 1.8 | 4.0 |
| SODIUM COCOAMPHOACETATE | | | | | 2.0 | | | | 1.5 |
| DISODIUM PEG 4 COCAMIDO MIPA SULPHOSUCCINATE | | | | | | 1.0 | | | |

Fig. 1B

| Ingredients according to INCI nomenclature | A | B | C | D | E | F | G | H | I |
|---|---|---|---|---|---|---|---|---|---|
| Cocoamidopropylbetaine | | | | | | | | | |
| COCAMIDE DEA | | | | | | | | | |
| PEG-4 RAPESEED AMIDE | 2.0 | 1.5 | 1.5 | 1.5 | 1.5 | 2.0 | 2.0 | 2.0 | 1.5 |
| SODIUM TRIPOLYPHOSPHATE | 1.7 | 2.5 | 2.5 | 2.5 | 2.5 | | | | |
| PEG-8 | | | | | | 10.0 | | | |
| POLYGLYCERYL-3 CAPRATE (Tegosoft PC 31) | 1.5 | | 1.5 | 1.5 | 1.0 | 1.2 | 1.2 | 1.2 | 1.5 |
| POLYGLYCERYL-4 CAPRATE (Tegosoft PC 41) | | | | | | | | | |
| SUCROSE COCOATE Tegosoft LSE-65K soft) | | 1.5 | | | | | | | |
| PPG-11 STEARYL ETHER (Varonic APS) | 0.3 | | 0.3 | 0.3 | | 0.3 | 0.3 | 0.3 | 0.2 |
| PPG-3 MYRISTYL ETHER (Varonic APM) | | | | | 0.3 | | | | |
| Coco-Glucoside and Glyceryl Oleate (Lamesoft PO 65) | | | | | | | | | |
| CARBOXYMETHYLCELLULOSE | 0.7 | 0.6 | 0.6 | 0.6 | 0.7 | 0.7 | 0.7 | 0.7 | 0.7 |
| XANTHAN GUM | | | | | 0.3 | | | | |
| Stearic acid | | | | | | | | | |
| SODIUM CHLORIDE | 1.5 | 1.5 | 1.5 | 0.5 | 0.5 | 0.6 | 1.5 | 1.5 | 0.6 |
| Oleic Acid | 0.6 | | | | | | 0.6 | 0.9 | |

Fig. 1C

| Ingredients according to INCI nomenclature | A | B | C | D | E | F | G | H | I |
|---|---|---|---|---|---|---|---|---|---|
| SODIUM BENZOATE | 0.6 | 0.6 | 0.6 | 0.6 | 0.6 | 0.6 | 0.6 | 0.6 | 0.6 |
| POTASSIUM SORBATE | 0.3 | 0.3 | 0.3 | 0.3 | 0.3 | 0.3 | 0.3 | 0.3 | 0.3 |
| PERFUME (FRAGRANCE) | 0.2 | 0.2 | 0.2 | 0.2 | 0.2 | 0.2 | 0.2 | 0.2 | 0.2 |
| CITRIC ACID | 1.4 | 1.3 | 1.3 | 1.3 | 1.5 | 1.4 | 0.5 | 0.5 | 0.5 |
| NaOH | | | | | | | | | |
| CI 77891 (titanium dioxide) | 0.5 | 0.5 | 0.5 | 0.5 | 0.2 | 0.5 | 0.5 | 0.5 | 0.4 |

Fig. 1D

| Ingredients according to INCI nomenclature | J | K | L | M | N | O | P |
|---|---|---|---|---|---|---|---|
| AQUA (WATER) | 79.5 | 30.6 | 30.6 | 65.8 | 66.5 | 64.8 | 75.2 |
| JUGLANS REGIA SHELL POWDER | 0.0 | 30.0 | 20.0 | 12.0 | 8.0 | 12.0 | 0.0 |
| QUARTZ SAND | | | | | | | |
| Sodium carbonate | | | | | | | |
| Rapeseed oil | | | | | | | |
| Sodium lauryl sulphate | | | | | | | |
| LAURETH-6 | 3.0 | 20.0 | 2.0 | 6.0 | 9.0 | 9.0 | 6.0 |
| LAURETH-5 | | | | | | | |
| POLOXAMER 407 (EO/PO block polymer – Pluronic) | | | | | | | |
| ALKYL POLYGLUCOSIDE | | | | | | | |
| SODIUM LAURETH SULPHATE | 6.0 | 6.0 | 30.0 | 3.3 | 3.3 | 3.3 | 5.0 |
| SULPHATED CASTOR OIL | 4.0 | 4.0 | 8.0 | 2.8 | 2.8 | 2.8 | 2.5 |
| DISODIUM LAURETH SULPHOSUCCINATE | 1.5 | | | 1.8 | 1.8 | 1.9 | 3.0 |
| SODIUM COCOAMPHOACETATE | | | | | | | |
| DISODIUM PEG 4 COCAMIDO MIPA SULPHOSUCCINATE | | | | | | | |
| Cocoamidopropylbetaine | | | | | | | |
| COCAMIDE DEA | | | 2.5 | 2.0 | | | |
| PEG-4 RAPESEED AMIDE | 2.5 | 2.5 | | | 1.5 | 1.5 | 3.5 |

Fig. 1E

| Ingredients according to INCI nomenclature | J | K | L | M | N | O | P |
|---|---|---|---|---|---|---|---|
| SODIUM TRIPOLYPHOSPHATE | | | | | | | |
| PEG-8 | | | | | | | |
| POLYGLYCERYL-3 CAPRATE (Tegosoft PC 31) | 0.2 | 3.0 | 3.0 | | 1.5 | | 1.2 |
| POLYGLYCERYL-4 CAPRATE (Tegosoft PC 41) | | | | | | 1.2 | |
| SUCROSE COCOATE Tegosoft LSE-65K soft) | | | | 1.5 | | | |
| PPG-11 STEARYL ETHER (Varonic APS) | | 0.6 | 0.6 | | | | |
| PPG-3 MYRISTYL ETHER (Varonic APM) | | | | | 0.3 | 0.3 | 0.3 |
| Coco-Glucoside and Glyceryl Oleate (Lamesoft PO 65) | | | | | | | |
| CARBOXYMETHYLCELLULOSE | 0.7 | 0.7 | 0.7 | 0.7 | 0.7 | 0.7 | 0.7 |
| XANTHAN GUM | | | | | | | |
| Stearic acid | 0.6 | 0.6 | 0.6 | 1.5 | 0.6 | 0.6 | 0.6 |
| SODIUM CHLORIDE | | | | 0.6 | | | |
| Oleic Acid | | | | | | | |
| SODIUM BENZOATE | 0.6 | 0.6 | 0.6 | 0.6 | 0.6 | 0.6 | 0.6 |
| POTASSIUM SORBATE | 0.3 | 0.3 | 0.3 | 0.3 | 0.3 | 0.3 | 0.3 |

Fig. 1F

| Ingredients according to INCI nomenclature | J | K | L | M | N | O | P |
|---|---|---|---|---|---|---|---|
| PERFUME (FRAGRANCE) | 0.2 | 0.2 | 0.2 | 0.2 | 0.2 | 0.2 | 0.2 |
| CITRIC ACID | 0.5 | 0.5 | 0.5 | 0.5 | 0.5 | 0.5 | 0.5 |
| NaOH | | | | | | | |
| CI 77891 (titanium dioxide) | 0.4 | 0.4 | 0.4 | 0.4 | 0.4 | 0.4 | 0.4 |

Fig. 1G

| Ingredients according to INCI nomenclature | Q to B | R to G | S | T | U |
|---|---|---|---|---|---|
| AQUA(WATER) | 59.0 | 61.9 | 35.7 | 40.9 | 56.6 |
| JUGLANS REGIA SHELL POWDER | 15.0 | 2.0 | | 13.0 | 15.0 |
| QUARTZ SAND | | | 35.0 | | |
| Sodium carbonate | | | 4.3 | | |
| Rapeseed oil | | | | 20 | 10 |
| Sodium lauryl sulphate | | | 20.2 | | |
| LAURETH-6 | 6.5 | 6.0 | | 11.0 | 7.0 |
| LAURETH-5 | | | | | |
| POLOXAMER 407 (EO/PO block polymer – Pluronic) | | | 0.5 | | |
| ALKYL POLYGLUCOSIDE | 3.1 | 3.3 | 0.4 | 7.5 | 3.0 |
| SODIUM LAURETH SULPHATE | 2.8 | 2.5 | | 2.1 | 3.5 |
| SULPHATED CASTOR OIL | 2.1 | 1.8 | | | |
| DISODIUM LAURETH SULFOSUCCINATE | | | | | |
| SODIUM COCOAMPHOACETATE | | | 0.5 | | |
| DISODIUM PEG 4 COCAMIDO MIPA SULPHOSUCCINATE | | | 0.5 | | |
| Cocoamidopropylbetaine | | | | | |
| COCAMIDE DEA | 1.5 | 2.0 | | | |
| PEG-4 RAPESEED AMIDE | | | | | |

Fig. 1H

| Ingredients according to INCI nomenclature | Q to B | R to G | S | T | U |
|---|---|---|---|---|---|
| SODIUM TRIPOLYPHOSPHATE | 2.5 | | | | |
| PEG-8 | | | | | |
| POLYGLYCERYL-3 CAPRATE (Tegosoft PC 31) | | | | | |
| POLYGLYCERYL-4 CAPRATE (Tegosoft PC 41) | | | | | |
| SUCROSE COCOATE Tegosoft LSE-65K soft) | | | | | |
| PPG-11 STEARYL ETHER (Varonic APS) | | | | | |
| PPG-3 MYRISTYL ETHER (Varonic APM) | | | 5.0 | | |
| Coco-Glucoside and Glyceryl Oleate (Lamesoft PO 65) | 3.0 | 2.4 | | | |
| CARBOXYMETHYLCELLULOSE | 0.4 | 0.7 | | 0.7 | 0.7 |
| XANTHAN GUM | 0.3 | 0.3 | | 0.3 | 0.3 |
| Stearic acid | | | 1 | | |
| SODIUM CHLORIDE | 1.5 | 1.2 | | 2.4 | 0.6 |
| Oleic Acid | | 1.4 | | | 1.2 |
| SODIUM BENZOATE | 0.6 | 0.6 | | 0.6 | 0.6 |
| POTASSIUM SORBATE | 0.3 | 0.3 | | 0.3 | 0.3 |
| PERFUME (FRAGRANCE) | 0.2 | 0.2 | 0.2 | 0.2 | 0.2 |

Fig. 11

| Ingredients according to INCI nomenclature | Q to B | R to G | S | T | U |
|---|---|---|---|---|---|
| CITRIC ACID | 1.0 | 1.5 | 1.2 | 0.6 | 0.6 |
| NaOH | 0.5 | 1.2 | 1.7 | 0.4 | 0.4 |
| CI 77891 (titanium dioxide) | | | | | |

SKIN AND HAND CLEANING COMPOSITIONS WITH HYDROPHILIC EMOLLIENTS

BACKGROUND OF THE INVENTION

FIELD OF THE INVENTION

The invention relates to skin and hand cleaning compositions with hydrophilic emollients with improved dermatological compatibility and to the use of the compositions for removing extreme soilings.

DESCRIPTION OF THE BACKGROUND

Skin and hand cleaning compositions are used extensively in industry as so-called rough hand cleaners, in particular wherever stubborn soilings occur, which are caused by paints, fats, oils, lubricants, metal dusts, graphite, soot and the like.

The more often such products are applied to the skin in the industrial sector (up to 6 times and more often per day), the more considerable the disadvantageous effects of the abrasives, surfactants or surfactant mixtures and in particular also solvents, such as, for example, aliphatic hydrocarbons, terpenes, carboxylic acid esters of the type dimethyl adipate, dimethyl glutarate, dimethyl succinate (DBE) and di-n-butyl adipate or diisopropyl adipate, which have been described in DE 43 35933 A1, contained in these rough hand cleaners come to the fore, namely the degreasing and drying-out of the skin through the destruction of the hydro-lipid mantle of the skin. This then leads to increased absorption of toxic and allergenic substances or to attack by microorganisms or consequently to toxic or allergenic skin reactions.

To avoid the aforementioned skin problems, a large number of formulations for rough hand cleaners have been proposed in the patent literature. Thus, for example, WO 99/06021 describes hydrous so-called "waterless hand cleaner" formulations which have a water content of from 75 to 99% by weight, up to 25% by weight of a fatty acid ester or mixtures of such esters, and at least one surfactant. Compared with the aforementioned products containing organic solvents, such formulations constitute a significant improvement, particularly from a toxicological point of view. Nevertheless, the improved skin compatibility and the improved protection against the drying-out of skin was accompanied by a loss in cleaning effect compared to solvent-containing rough hand cleaners.

DE 197 48 921 A1 relates to hydrous liquid, pasty or creamy hand cleaning compositions, in particular rough hand cleaning compositions with an abrasive which have a content of from 10 to 30% by weight of at least one vegetable oil, selected from the group of triglycerides, saturated and/or unsaturated fatty acids, of from 10 to 30% by weight of at least one surfactant from the group fatty alcohol ethoxylates, fatty alcohol ether sulphates and/or castor oil sulphonates, and also 10 to 65% by weight of water, in each case based on the composition of the cleaning compositions. As rough hand cleaners, these compositions comprise 1 to 30% by weight of at least one abrasive in the composition. The rough hand cleaners described therein are very highly skin compatible from a dermatological point of view and only have slight drying-out of the skin even upon repeated daily use.

EP 1 152 051 A2 discloses skin-mild hand washing pastes, fatty acid alkyl esters being used in combination with emulsifiers, preferably fatty alcohol ethoxylates. The refatting agents used are additionally partial glycerides. Although the refatting agents are described extensively in this printed specification, the examples refer only to emulsions with 20 to 30% by weight of fatty acid esters and additionally 10% by weight of a mixture of cocoglycosides and glyceryl oleate (Lamesoft PO65). It is to be assumed that the refatting effect is based, similarly to the hand cleaning compositions described in DE 197 48 921 C2, on the content of fatty acid esters. Nevertheless, the hand washing pastes according to EP 1 152 051 A2 also lead to drying-out of the skin upon frequent use.

DE 199 16 036 A1 describes hand washing pastes comprising anionic surfactants, abrasive bodies and partial glycerides, in particular oleic acid monoglycerides, and the use of such partial glycerides for improving the skin feel. However, in the examples, only a mixture of cocoglycosides and glyceryl oleate (Lamesoft PO65) is used. Although the hand washing pastes described in this laid-open specification are said to lead to a subjective improvement in skin feel, no experimental data for this are given which could demonstrate such an improvement in the skin condition.

Nevertheless, even such a subjective improvement in skin feel upon frequent use of such rough hand cleaners is perceived by the users as skin-drying despite the fact that the rough hand cleaners according to DE 197 48 921 A1 contain up to 30% by weight of vegetable oils, preferably rapeseed oil as refatting agent or hydrophobic emollient. The same is true for EP 1 152 051 A1 which contain up to 40% by weight of fatty acid allkyl esters as hydrophobic emollient. Moreover, with regard to the formulations described in DE 199 16 036 A1 which contain partial glycerides, it is to be established that these lead to an increase in the drying-out of the skin upon frequent use.

There is thus still a need for mild skin and hand cleaning compositions which ensure a very good cleaning effect even on the most stubborn of skin soilings, coupled with very good skin compatibility. In particular, these rough hand cleaners should produce a very good skin feel during washing, this very good skin impression on account of the slight drying-out of the skin remaining perceptible to the user for some time even after washing, and thus increasing the acceptance by the users with regard to the use of rough hand cleaners.

BRIEF SUMMARY OF THE INVENTION

It was therefore an object to provide such skin and hand cleaning compositions, in particular rough hand cleaning compositions. This object was surprisingly achieved by skin and hand cleaning compositions which have a content of at least 0.1% by weight of at least one hydrophilic emollient with an HLB value of $\geq 10$, polyol esters being particularly preferred as hydrophilic emollients.

It is essential to the invention for these skin and hand cleaning compositions that the hydrophilic emollients have an HLB value of $\geq 10$. The HLB value is a measure of the water solubility or oil solubility of predominantly nonionic surfactants and emulsifiers, for example in cosmetic products, and thus describes the hydrophilic part and the lipophilic part of a chemical compound. For example, an HLB value of 0 corresponds to a purely lipophilic compound. By contrast, a chemical compound with an HLB value of 20 has only hydrophilic parts. Thus, water-in-oil emulsions are assigned HLB values from 3 to 8, whereas oil-in-water emulsions have HLB values from 8 to 18, and detergents have HLB values from 13 to 15 (see also RÖMPP—Chemistry Lexicon, 10th edition, page 1764, keywords: HLB system, HLB value—and literature cited therein).

For the invention present here, emollients with an HLB value from 1 to 8 are referred to as hydrophobic, those with a value from 8 to 10 as neutral, and those with a value ≧10 as hydrophilic.

In contrast to the predominantly lipophilic emollients used hitherto in the prior art, the hydrophilic emollients according to the invention have an HLB of ≧10, preferably ≧12. For example, the mixture of cocoglycosides and glyceryl oleate (Lamesoft PO65) described in DE 199 16 036 A1 has an HLB value of 9 and fatty acid esters have a yet significantly lower HLB value. It was therefore entirely surprising, although the hydrophilic emollients according to the invention are significantly more hydrophilic and thus also have significantly better solubility in water and are thus easier to wash off than the emollients used in the abovementioned prior art, i.e. it thus does not result in a refatting in the actual sense, that the skin feel after frequent use is subjectively not only described as less dry by the users, but the improved skin condition can also be quantified objectively by means of corneometer measurements, as will be shown in the experimental section.

DETAILED DESCRIPTION OF THE INVENTION

According to the invention, the skin and hand cleaning compositions according to the invention preferably have a content, in each case based on the total composition of the cleaning composition, of the components
a.) at least 0.1% by weight of at least one hydrophilic emollient, preferably a polyol ester,
b.) 2 to 40% by weight of at least one surfactant selected from the group of fatty alcohol ethoxylates, fatty alcohol ether sulphates and salts of sulphated and/or sulphonated fatty acids,
c.) 30 to 90% by weight of water,
d.) 0 to 30% by weight of one or more cleaning boosters selected from the group of polyols, polyethers, polyphosphates and phosphates,
e.) 0 to 30% by weight of one or more abrasives,
f.) 0 to 1.0% by weight of propoxylated fatty alcohols,
g.) if desired one or more viscosity-forming agents,
h.) if desired further cosmetic auxiliaries, additives and/or active ingredients,
the sum of components a.) to h.) being 100% by weight.

The polyol esters to be used as component a.), which are to be regarded as hydrophilic emollient in the skin and hand cleaning compositions according to the invention, are, for example, partial glycerides, in particular polyglyceryl partial esters. According to the invention, preference is given to polyglyceryl partial esters of the general formula $$R_1-\overset{O}{\underset{\|}{C}}-O-CH_2-\underset{\underset{OH}{|}}{CH}-CH_2-(O-CH_2-\underset{\underset{OH}{|}}{CH}-CH_2)_n-OH$$

where
$R_1$=linear, branched or cyclic, saturated or unsaturated alkyl or alkenyl radical having 6 to 18 carbon atoms and
n=an integer from 1 to 9.

The linear, branched or cyclic, saturated or unsaturated alkyl or alkenyl radical has in particular 6 to 16 and particularly preferably 8 to 12 carbon atoms, where preferably n=1 to 5, in particular n=1 to 3. Furthermore, it is also possible to use polyglycerol esters with another structure, e.g. based on 1,2- or 1,3-linked polyglycerols, and also polyglycerol ethers.

The polyglyceryl partial esters or polyglycerol fatty acid esters particularly preferred according to the invention are, for example, polyglyceryl-3 caprate or polyglyceryl-4 caprate, which are available from Degussa under the names TEGOSOFT® PC31 and TEGOSOFT® PC41.

Polyol esters for the purposes of the present invention are furthermore polyethylene glycol esters, such as, for example, PEG-7 glyceryl cocoate, which is available from Croda Chemicals Europe Ltd. under the name Glycerox HE.

As hydrophilic emollients, component a.) in the skin and hand cleaning compositions according to the invention can also contain polysaccharide esters and/or polysaccharide ethers and/or polysaccharide glycosides with an HLB ≧10, preferably ≧12. Preference is given to sucrose esters, as can be obtained, for example, from Degussa GmbH under the names TEGOSOFT® LSE 65 K and TEGOSOFT® LSE 65 K Soft.

The fraction of component a.) in the skin and hand cleaning compositions according to the invention can be up to 10% by weight, preferably 0.1 to 5% by weight, particularly preferably 0.3 to 3% by weight, based on the composition of the cleaning composition. The hydrophilic emollients can be present on their own or in multiples as component a.) in the skin and hand cleaning compositions according to the invention.

The fatty alcohol ethoxylates that can be used as component b.) preferably have the general formula $$R-O-(CH2-CH2-O)nH$$

where
R=saturated, unsaturated, branched or unbranched alkyl radical,
n=an integer from 1 to 11.

As saturated, unsaturated, branched or unbranched alkyl radical, preference is given to using R=$C_6$ to $C_{18}$, in particular $C_{10}$ to $C_{16}$ and particularly preferably $C_{11}$ to $C_{14}$, where preferably n=3 to 6, in particular n=5 to 7.

In the skin and hand cleaning compositions according to the invention, 2 to 40% by weight, preferably 3 to 20% by weight and particularly preferably 5 to 10% by weight, of fatty alcohol ethoxylates are present, based on the composition of the cleaning composition. In a preferred embodiment, the skin and hand cleaning compositions according to the invention contain 5 to 10% by weight, based on the composition of the cleaning composition, of laureth-6 as fatty alcohol ethoxylate.

The fatty alcohol ether sulphates of component b) that can be selected are in particular those of the general formula $$R-O-(CH2-CH2-O)_nSO_3X$$

where R=a $C_8$-$C_{18}$, preferably $C_{11}$-$C_{14}$, saturated or unsaturated, branched or unbranched alkyl radical, n=an integer from 1 to 6, preferably 1 to 4, and X=$Na^+$, $NH_4^-$ or $Mg^{2+}$, where sodium lauryl ether sulphate (where R=$C_{12}$, n=2-3 and X=$Na^-$) is particularly preferred.

According to the invention, the salts of sulphated and/or sulphonated fatty acids of component b.) used are alkali metal or alkaline earth metal salts of $C_8$-$C_{30}$, preferably $C_{10}$-$C_{22}$ fatty acids, particularly preferably castor oil sulphates, in particular $Na^+$ or $NH_4^-$ sulphates. Such castor oil sulphonates are available, for example, under the names Monobrilliantöl® (Stockhausen GmbH, Krefeld) or Standapol SCO® (Henkel KGaA, Düsseldorf).

The skin and hand cleaning compositions according to the invention which are free from organic solvents contain 30 to 90% by weight, based on the composition of the cleaning composition, preferably 40 to 80% by weight and particularly preferably 45 to 75% by weight of water as component c.).

Although the skin and hand cleaning compositions according to the invention exhibit a very good cleaning effect, such that the addition of cleaning boosters can be dispensed with, the skin and hand cleaning compositions can contain cleaning boosters from the class of polyols, polyethers, polyphosphates and phosphates as component d.) if desired for certain cleaning applications. Particular preference is given here to polyethers which are formed from the polymerization of ethylene glycol and 3 to 20 units, preferably 4 to 10 units. Preference is given to PEG-8, as can be obtained, for example, from Ineos under the name PEG 400. Furthermore, preference is given to polyphosphates, such as the pentasodium tripolyphosphate $Na_5P_3O_{10}$ (sodium tripolyphosphate), and the corresponding potassium and sodium potassium salts, which are available, for example, from BK Giulini.

The skin and hand cleaning compositions according to the invention exhibit a very good cleaning effect, such that the addition of abrasives to these cleaning compositions can be dispensed with. Nevertheless, the skin and hand cleaning composition can, if desired, contain abrasives as optional component e.) for certain cleaning applications. The fraction of abrasive or abrasives can then be 0 to 30% by weight, based on the composition of the cleaning composition, preferably 5 to 25% by weight, particularly preferably 5 to 25% by weight. Preferred abrasives to be used are, for example, synthetic abrasives based on polyethylene or polyurethane, abrasives based on natural kernel and/or shell flours, in particular walnut shell, almond shell, hazelnut shell, olive kernel, apricot kernel and cherry kernel flour or any desired mixtures of these shell and kernel flours and beads made of waxes, such as, for example, jojoba waxes, walnut shell flour bleached with hydrogen peroxide being particularly preferred.

Particular preference is given to the synergistic use of small amounts of propoxylated fatty alcohols as component f.) up to 1.0% by weight, based on the composition of the cleaning composition, with component a.). Use is made of propoxylated fatty alcohols, which are available as addition products of propylene oxide onto caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol and erucyl alcohol, and technical-grade mixtures thereof, in the form of their salts, in particular sodium and/or magnesium salts. Preference is given to the use of adducts of, on average, 1 to 20 mol of propylene oxide onto the desired fatty alcohols. According to the invention, particular preference is given to propoxylated fatty alcohols, as are available, for example, from Degussa GmbH under the name VARONIC® APS (PPG-11 stearyl ether) or VARONIC® APM (PPG-3 myristyl ether). 0.01 to 1% by weight, preferably 0.1 to 0.7% by weight, are used.

Moreover, in a further embodiment of the invention, the skin and hand cleaning compositions according to the invention can if desired contain one or more viscosity-forming agents, such as, for example, organophilic and/or hydrophilic sheet silicates as component g.), in particular bentonites, polysaccharides, such as, for example, cellulose, guar flour and/or xanthans, modified polysaccharides, preferably cellulose ethers, carboxyalkylcellulose and/or hydroxyalkylcelluloses, preferably hydroxyethylcellulose and/or inorganic electrolytes, preferably sodium chloride and/or magnesium sulphate. According to the invention, particular preference as component g.) is given to carboxymethylcelluloses (e.g. Walocel CRT—Wolff Cellulosics, Walsrode), which, moreover, bring about the very good foam-stabilizing effect while using the skin and hand cleaning compositions according to the invention. The skin and hand cleaning compositions according to the invention particularly advantageously contain 0.1 to 1.5% by weight, based on the total composition of the cleaning composition.

Furthermore, the skin and hand cleaning compositions according to the invention can if desired contain further cosmetic auxiliaries, additives and/or active ingredients, for example pH regulators, stabilizers, preferably cetearyl alcohol and/or hydrogenated castor oils such as, for example, trihydroxystearin, fragrances, preservatives, preferably organic acids and antioxidants, such as, for example, vitamin E acetate, as component h.). Preferably, it is also possible to use oily or aqueous care components, such as, for example, bisabolol, aloe vera, panthenol, sodium PCA, jojoba oil, creatine etc., in order to emphasize the care effect.

Moreover, the use of alkoxylated amides as component h.) is particularly advantageous, such as, for example, PEG-4 rapeseed amide (Amidet N—Biesterfeld Spezialchemie GmbH, Hamburg), preferably 0.5 to 5% by weight, particularly preferably 1 to 4% by weight, based on the total composition of the cleaning composition as stabilizer.

The production of the skin and hand cleaning compositions according to the invention, in particular rough hand cleaners, usually takes place by means of known devices in a batch or continuous process, the skin and hand cleaning compositions preferably being obtained as creamy compositions or as flowable viscous pastes. Suitable devices are heatable vessels with stirrer, continuous mixers such as extruders and dispersers.

It has surprisingly been found that despite dispensing with the use of hydrophobic emollients such as, for example, vegetable oils in the case of the rough hand cleaners according to DE 197 48 921 C2, through the use of hydrophilic emollients corresponding to component a.) in the skin and hand cleaning compositions according to the invention, a significantly increased skin care effect and also an improved skin impression can be observed without thereby resulting in an impairment of the cleaning effect.

The skin and hand cleaning compositions according to the invention exhibit a very good cleaning effect, coupled with very good skin compatibility and low drying-out of the skin. It is particularly advantageous that the skin and hand cleaning compositions according to the invention produce a very good skin feel during washing. Moreover, it was observed that even with slight oil contamination, the skin and hand cleaning compositions according to the invention foam to a considerably greater degree than rough hand cleaners of the prior art. The skin feel after washing is also considerably more pleasant after some time on account of the lower drying-out of the skin.

The invention is described by the following examples and investigations, such as skin compatibility test with the help of the Duhring chamber test, drying-out of the skin using the corneometer and cleaning power with the help of the hand washing test.

Test Methods

Determination of the HLB Value

The HLB value is determined by preparing a 5% strength dispersion/solution of the substance to be tested, here the hydrophilic emollient, in water, and determining the solubility in water. The assessment takes place visually: clouding, solubility, degree of dispersion. The HLB value is ascertained through comparison with solutions of emulsifiers whose HLB value is known. Ascertained HLB values:

| | |
|---|---|
| TEGOSOFT LSE 65 K soft | HLB: 12 |
| TEGOSOFT PC 31 | HLB: 14 |
| TEGOSOFT PC 41 | HLB: 16 |
| Lamesoft PO 65 | HLB: 9 |

HLB values according to manufacturer:

| | |
|---|---|
| Glycerox HE | HLB: 11 |

Duhring Chamber Test

The skin compatibility test takes place with the help of the Duhring chamber test according to P. J. Frosch, A. M. Kligman, Contact Dermatities 5, page 73, 1979; modified according to J. Kresken, W. S. Wassilew, H+G4, page 334, 1992; A. Klotz, Am. J. Cont. Derm., 2001, 12(1), page 52 and A. Klotz, M. Veeger, Pharm. Ztg. 2000, 145(35), page 47 to 51.

This method is an in vivo test model for checking the skin compatibility of various test products in direct comparison. The products to be tested are applied on the subjects in air-impermeable aluminium chambers on the volar side of their forearms on 4 consecutive days on the same test area in each case. What is assessed is skin irritations having formed, using the scale given below, and the application time 1 day after the last product application.

R=reddening (erythema): 0=no erythema, 4=severe erythema
S=scaling: 0=no scaling, 4=severe scaling
F=fissures: 0=no fissures, 3=severe fissures The assessment criteria arising are the
1. Irritation $\bar{x}$ as mean value of the sum of the irritation values R, S and F of n subjects
2. Application time $\bar{h}$ as mean value of the tolerated application time in hours of n subjects.

From these two values it is possible to calculate the relative skin compatibility (A value) according to the following formula:

$$\bar{A} = \frac{\bar{h}}{\sqrt{\bar{x}}}$$

It is thus possible to describe a relation between the application time and the irritation having formed during this time by a value. The table below can be used as an aid for assessing the skin compatibility of the tested products:

A value:

| | |
|---|---|
| >23 | excellent skin compatibility |
| 18-23 | very good skin compatibility |
| 13-18 | good skin compatibility |
| 8-13 | satisfactory skin compatibility |
| 3-8 | adequate skin compatibility |
| <3 | inadequate skin compatibility |

Testing the Drying-Out of the Skin Using the Corneometer

The corneometer measurement is a noninvasive capacitive measurement method for assessing the moisture state of the uppermost skin layers of the Stratum corneum. In subjects with healthy skin, this is largely determined by external influences.

Frequent cleaning of the skin leads to defatting of the skin and thus to a moisture reduction in the uppermost skin layers. Reduction in the moisture content of the skin represents a deterioration of the skin condition and causes an increased risk of eczema. This effect can be detected by measuring techniques using the corneometer, e.g. CM 825 from Courage & Khazaka Electronic GmbH, Köln.

Prior to the start of the test, the starting values ($C_0$) are determined, and at the end of the test the end values are determined ($C_n$).

The change in the skin moisture C is calculated as follows:

$$C = (C_n - C_0)$$

Negative values indicate an increase in skin moisture, positive values indicate a reduction in skin moisture.

Forearm Washing Test (FWT)

The forearm washing test (FWT) serves to test the skin compatibility of syndet preparations and hand cleaners. This test is particularly well suited for assessing test products containing abrasives. On account of the mechanically caused rubbing on the forearm, the various abrasives and abrasive concentrations can be tested with regard to their skin irritation.

The test is designed to simulate conditions encountered in practice and can follow a Duhring chamber test to verify the results.

On four consecutive days, controlled washings with the test products (0.5 g-1 g or 0.5 ml-1 ml syndet preparations or abrasive-containing hand cleaners) are carried out on the sensitive skin of the volar forearm.

The test area is wetted with tap water and then the product to be tested is applied to the skin and massaged in on the forearm over a large area for a total of 2 minutes. The other fields are treated in the same way with the respective test product. Assessment of the skin reactions is undertaken daily prior to the first washing and on day 5.

Assessment takes place visually and is if desired assisted by objective noninvasive measurement methods (e.g. TEWL, Corneometer, D-Squames®)

0=no reaction
1=weak, spotted (punctiform) reddening, slight scaling
2=moderate to medium reddening, slightly rough skin, average scaling
3=severe reddening in the centre of the area, very rough skin, marked scaling, punctuated erosions Testing the Cleaning Power with the Help of the Hand Washing Test The test model of the hand washing test with standardized soiling or paint gives information about the cleaning effect of the products to be tested. For relevance in practice, it is necessary that all subjects have a characteristic skin structure on the palms of the hands caused by manual work. Using one product at a time, the following test is carried out in the morning and afternoon:

Test Procedure with Water:
0.5 g of soiling (model soiling, practice soiling or paint) is distributed on the palm and the back of the hand and rubbed in
leave to dry for 1½ min
1.2 g of cleaning composition are applied and rubbed in
1 ml of water is added and wash for 30 s
add a further 1 ml of water and wash for 30 s
rinse under cold running water
visual assessment of the residual soiling (RS) on the back of the hand and the palm according to the scale, see below.

Test Procedure Without Water:
0.5 g of soiling (model soiling, practice soiling or paint) are distributed on the palm and on the back of the hand and rubbed in
leave to dry for 1½ min
1.2 g of cleaning composition are applied and rubbed in
using a cellulose paper, the soiling on the hand surfaces is removed together with the product
visual assessment of the residual soiling (RS) on the back of the hand and the palm according to the scale, see below.

0=clean 5=no cleaning effect (gradation in steps of 0.5 possible)

The percentage cleaning effect is calculated according to the following formula:

$$\text{cleaning effect } [\%] = \frac{10 - (\overline{RS}_{palm} + \overline{RS}_{back})}{10} * 100\%$$

$\overline{RS}_{palm}$=mean value of the residual soiling on palms of n measurement series (subjects)
$\overline{RS}_{back}$=mean value of the residual soiling on backs of hands of n measurement series (subjects)

Since the determination of the cleaning effect has a broader variation range, an absolute deviation of 5% between two measurement series is allowable.

Composition of a suitable model soiling:

| | |
|---|---|
| Engine oil: | 54.15% |
| Vaseline: | 18.05% |
| Wool wax: | 18.05% |
| Graphite: | 3.61% |
| Flame soot: | 5.42% |
| Iron oxide (Fe$_2$O$_3$): | 0.72% |

WORKING EXAMPLES

Figure 1A:
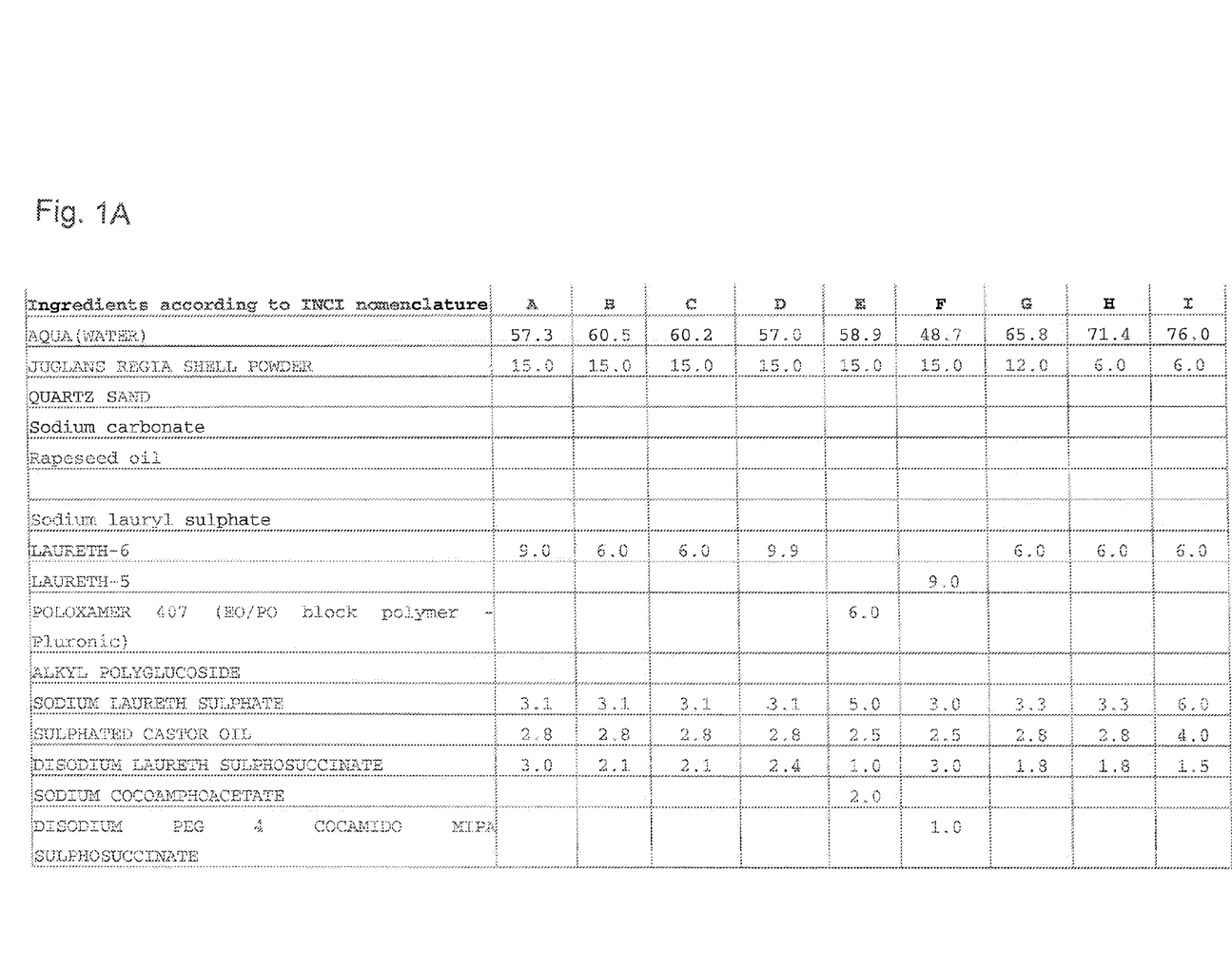
FIG. 1 represents Table 1.
Figure 1B:
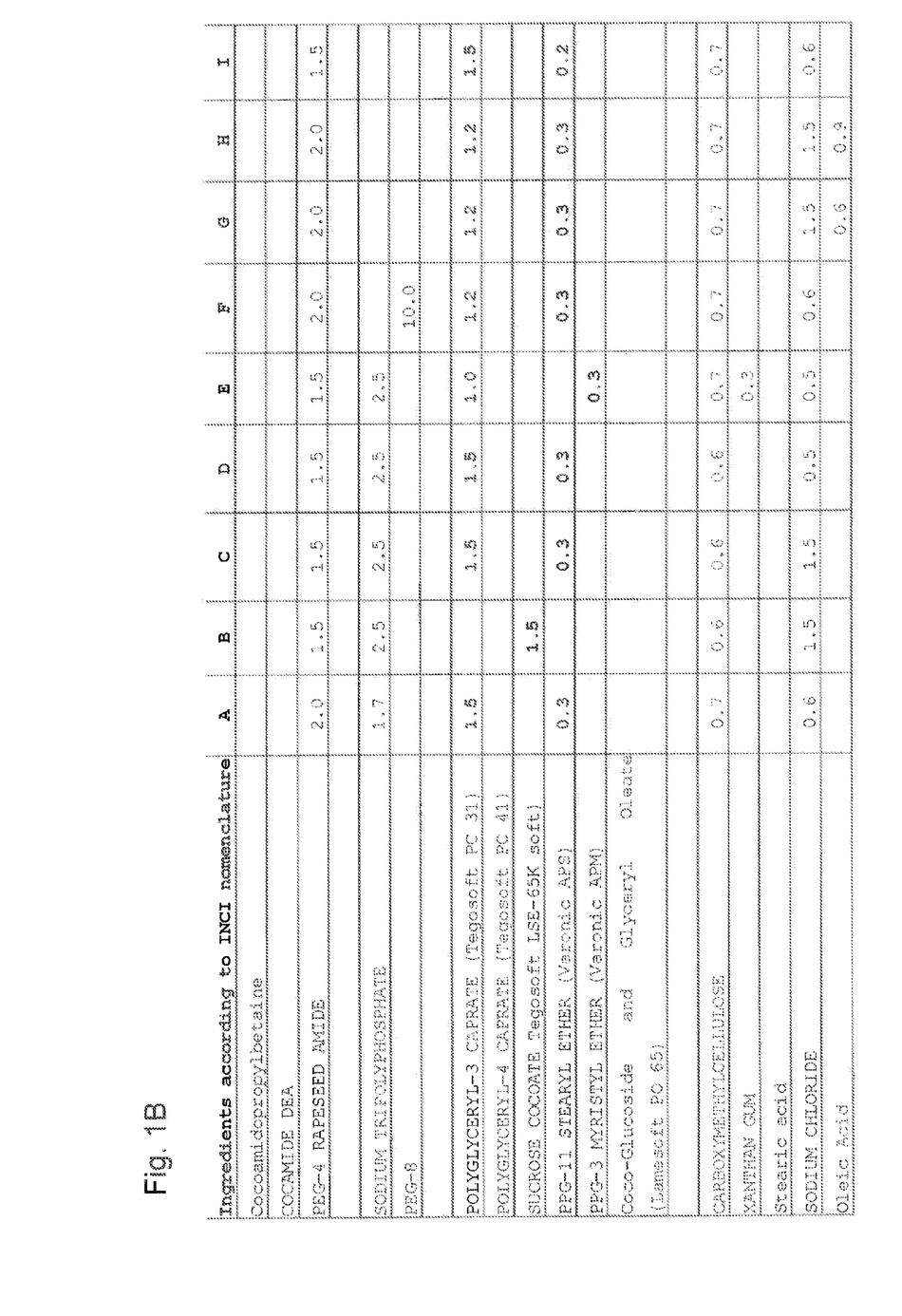
Figure 1C:
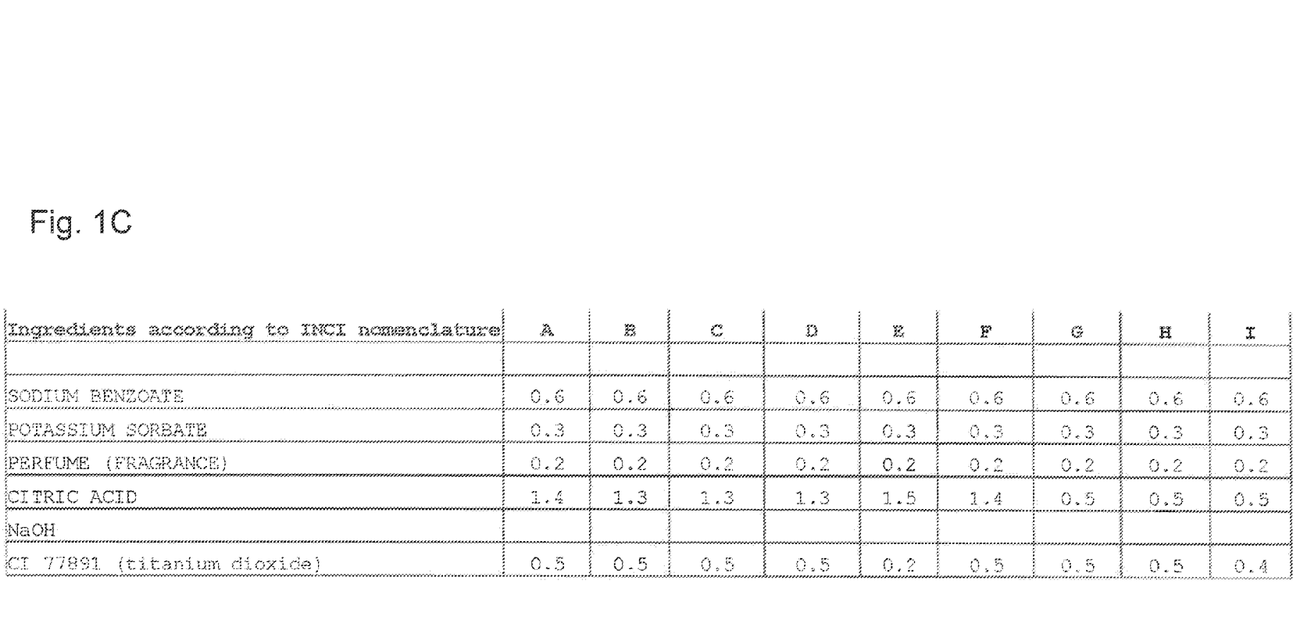
Figure 1D:
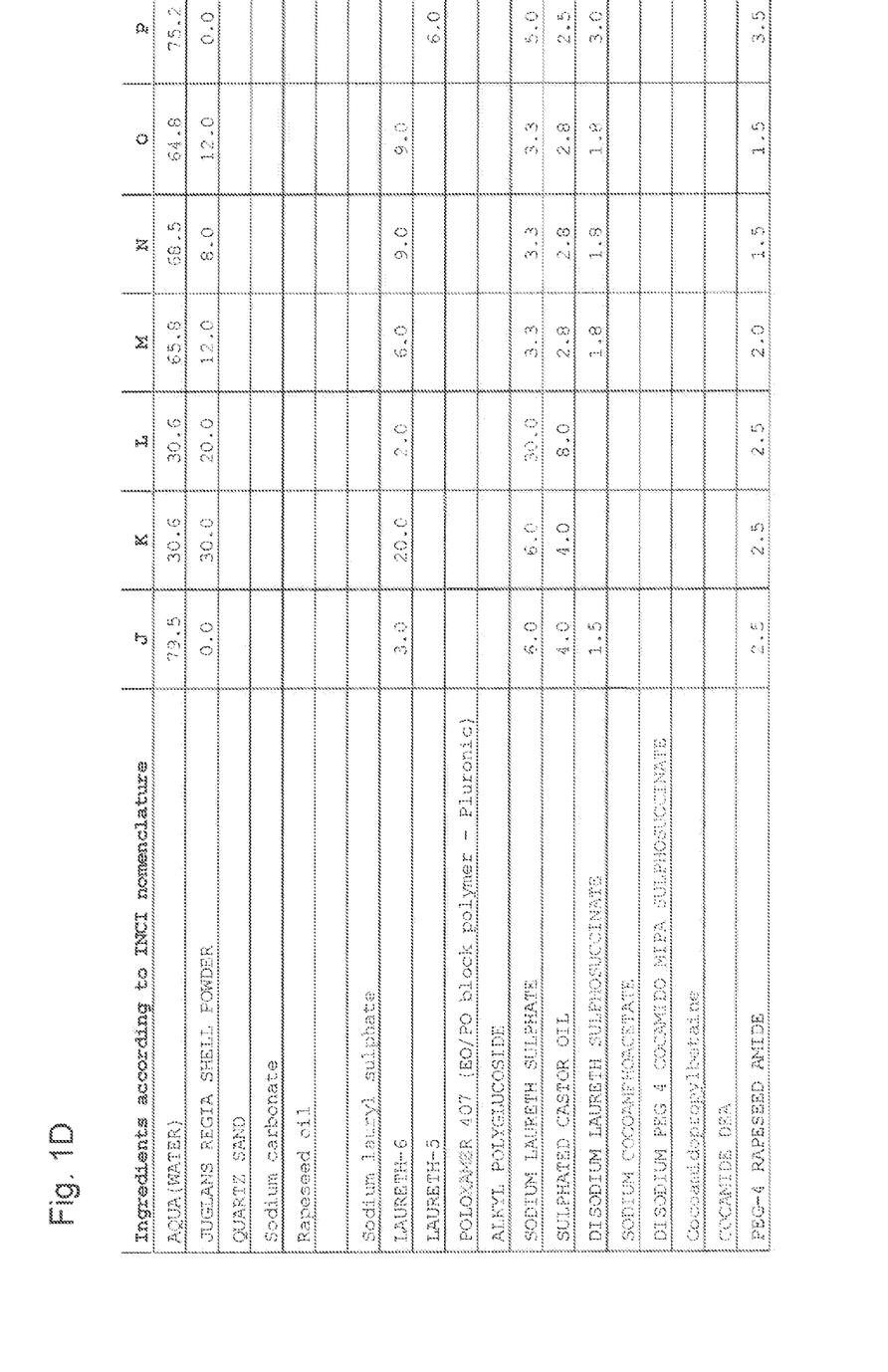
Figure 1E:
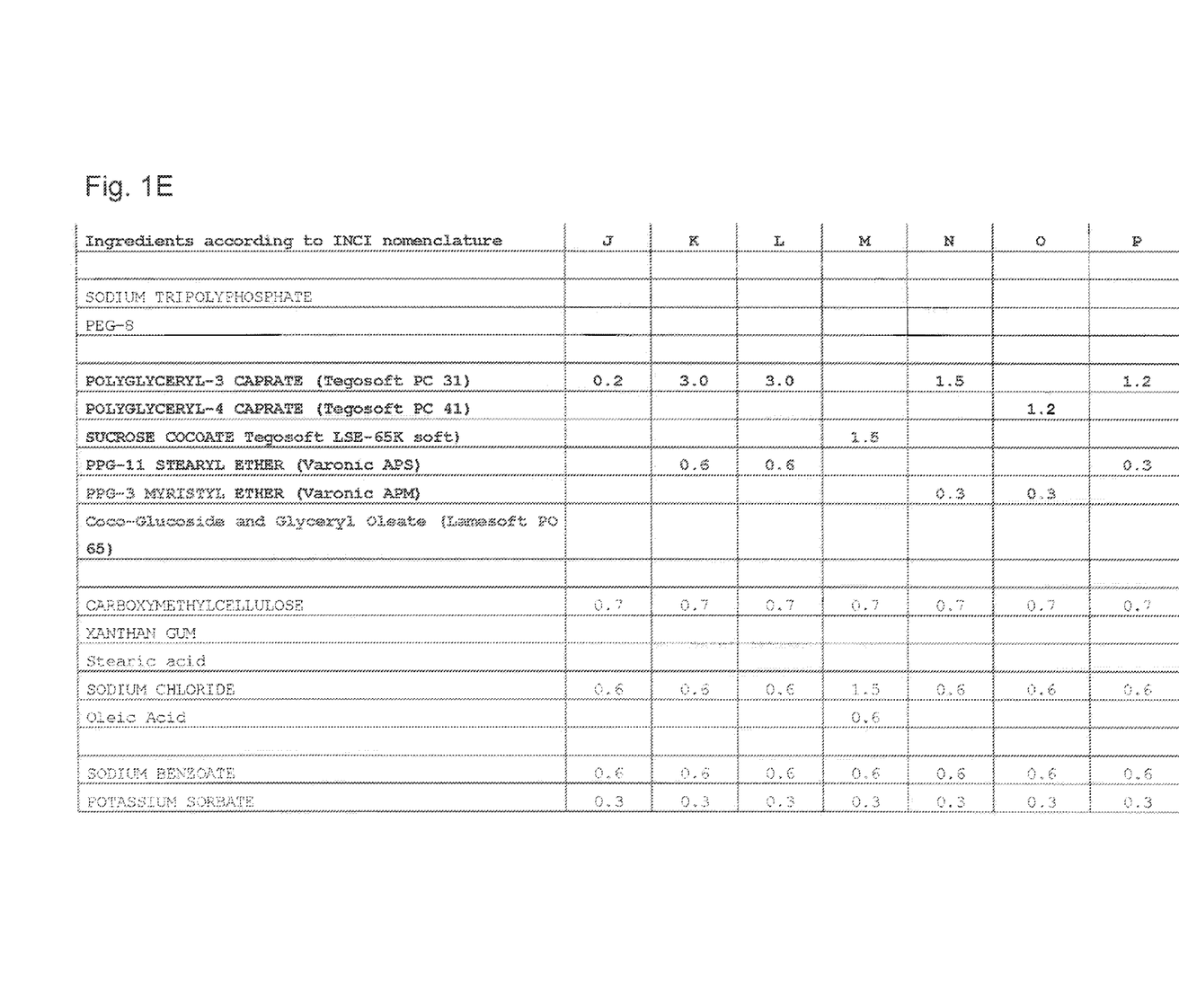
Figure 1F:
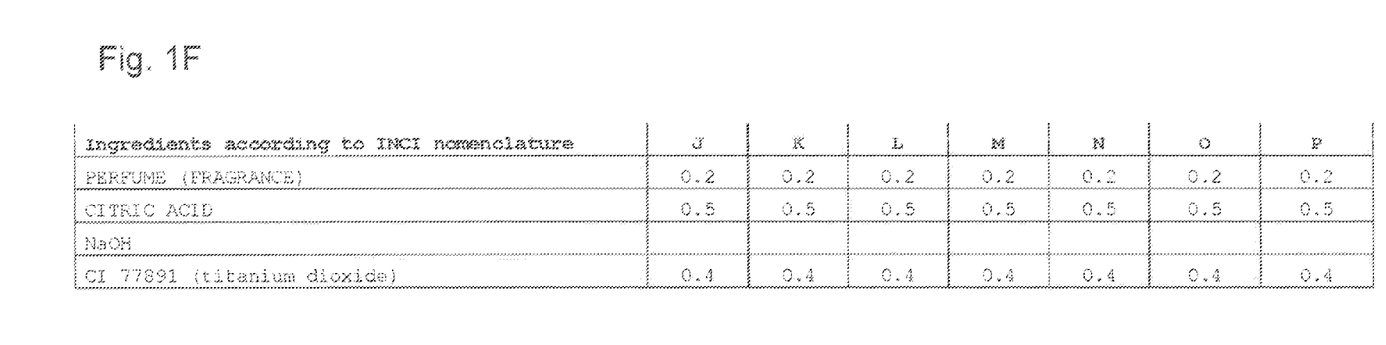
Figure 1G:
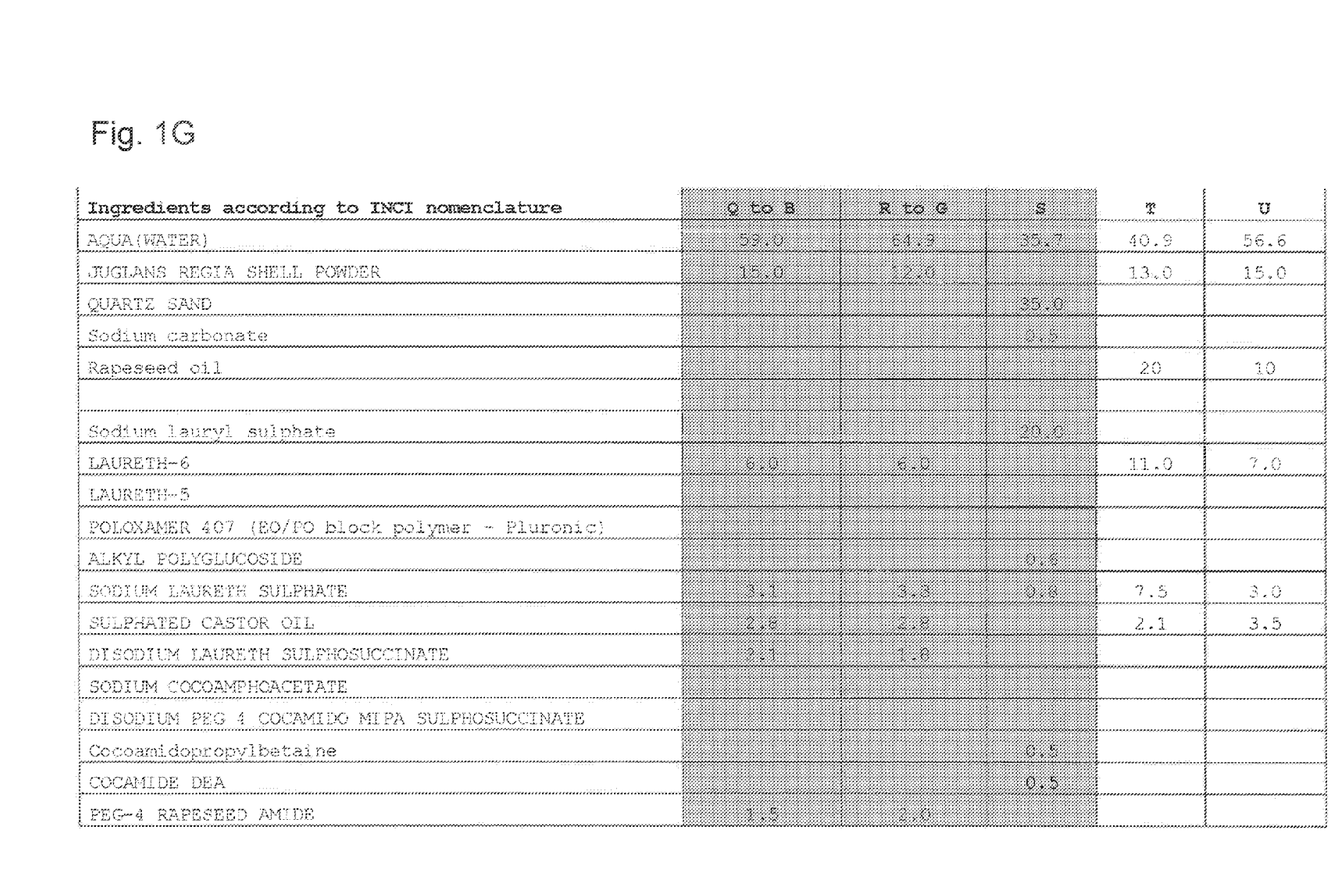
Figure 1H:
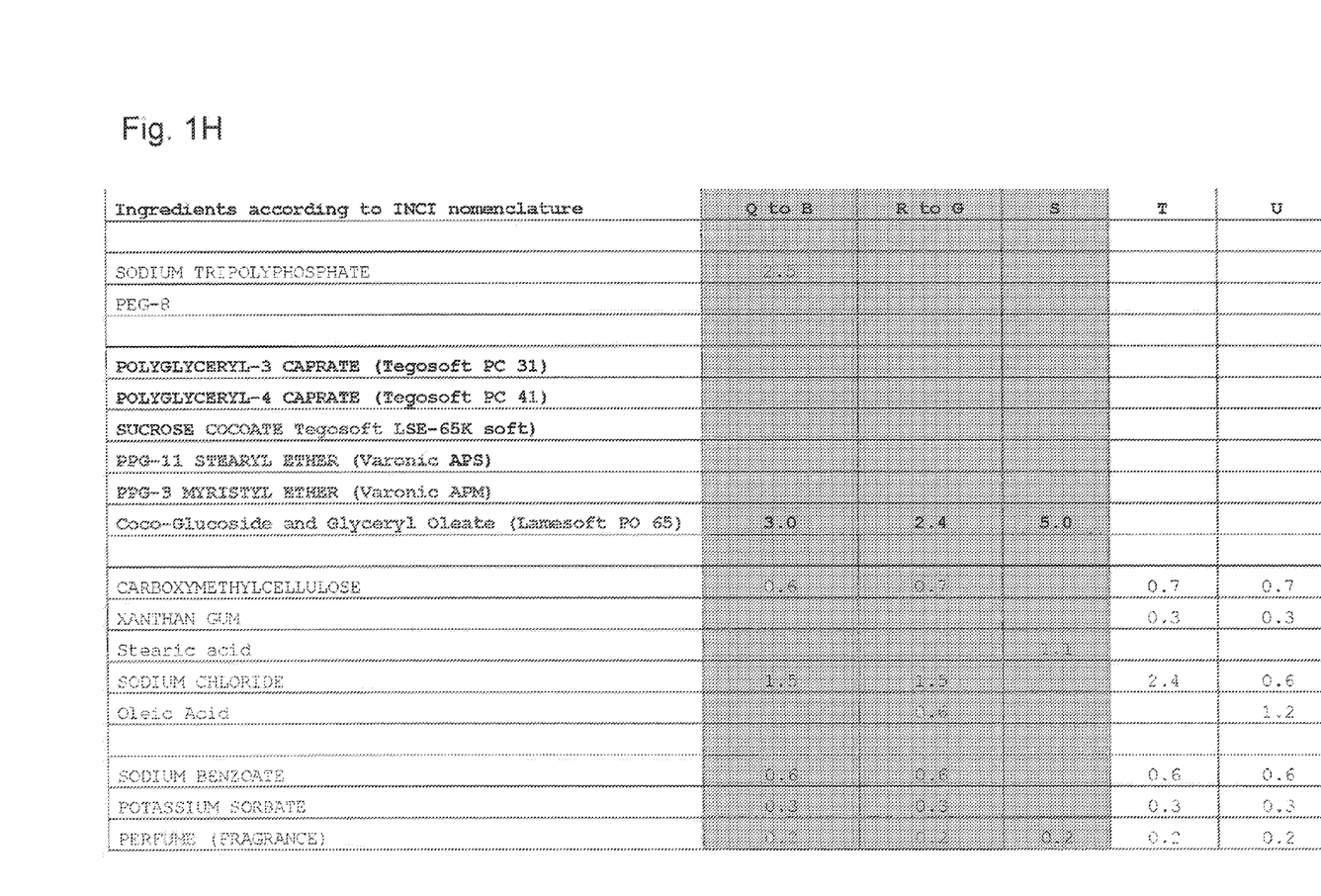
Figure 2:
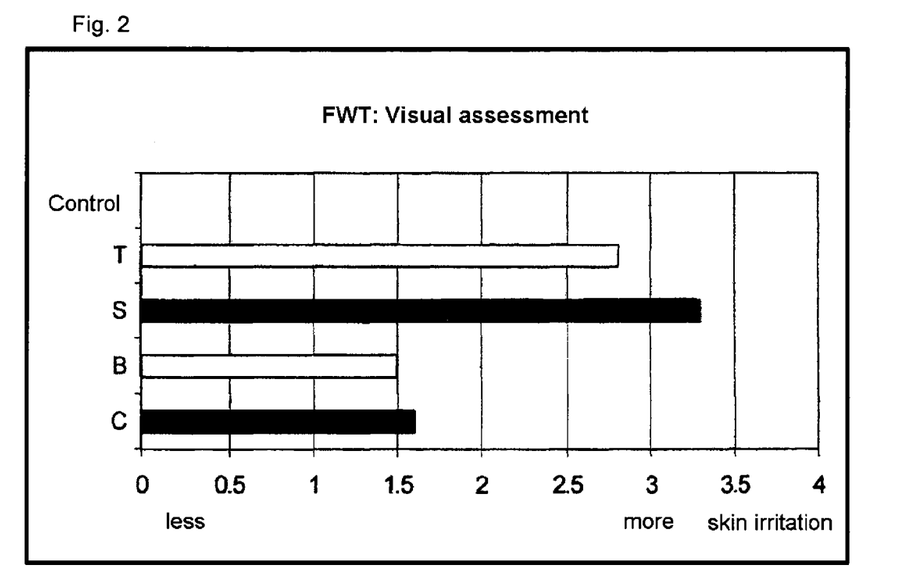
FIG. 2 represents results of a Forearm Washing Test by a visual assessment.
Figure 3:
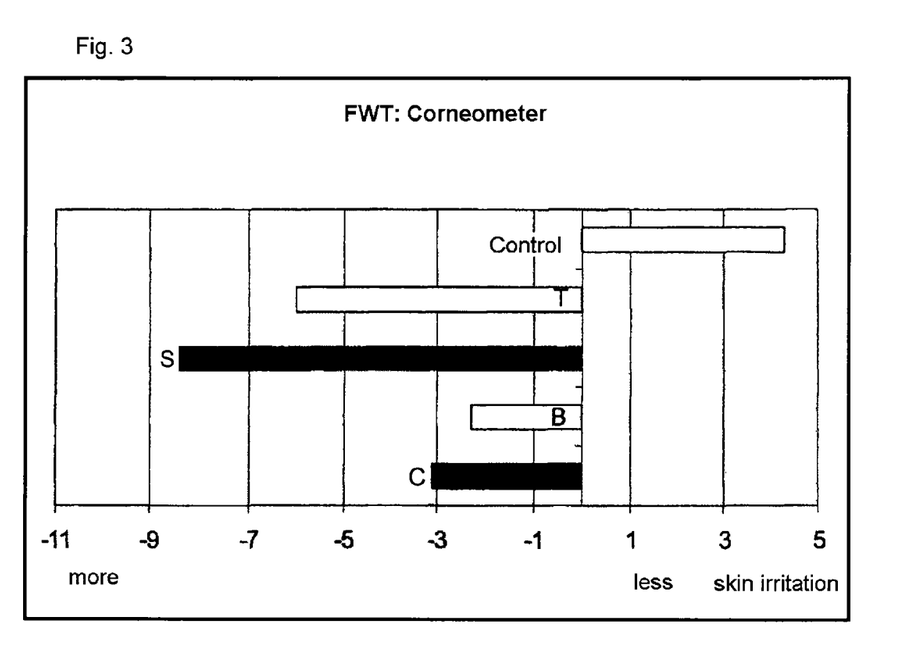
FIG. 3 represents results of a Forearm Washing Test by use of a Corneometer.
Figure 4:
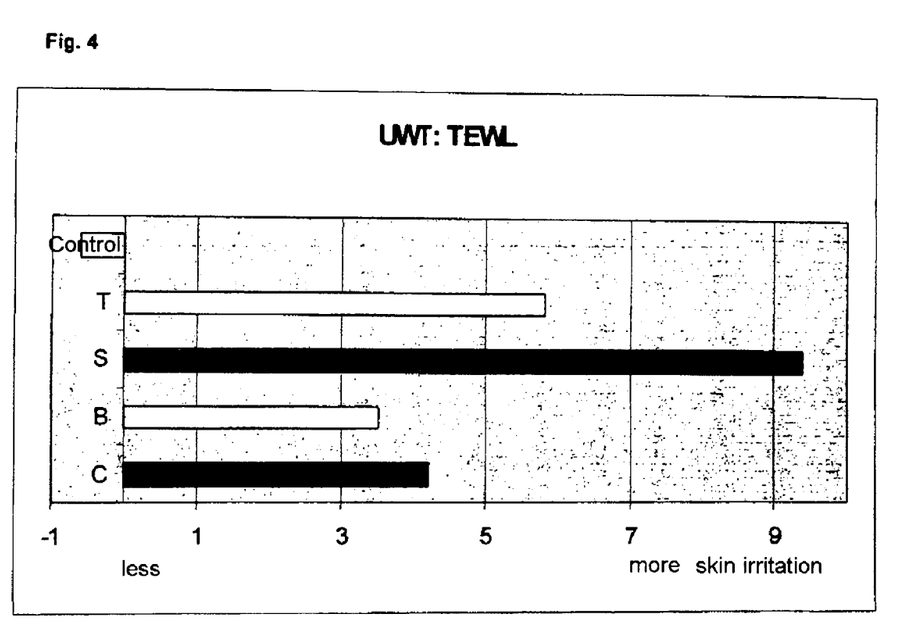
FIG. 4 represents results of an Unterarm Wasch Test, which is German for Forearm Washing Test.

Skin and hand cleaning compositions according to the compositions given in FIG. 1 were prepared by stirring together all of the components using the cold-cold, hot-cold or hot-hot methods customary in cosmetics up to at most 70° C. The compositions were characterized with regard to their skin compatibility, drying-out of the skin and cleaning effect towards a model soiling and paint.

In the described skin compatibility test, the example formulations A to P according to the invention have, compared to the solvent-free comparison formulation T, which is prepared according to DE 197 48 921 C2, a comparable, very good skin compatibility and, in the corneometer test, reduced drying-out of the skin after cleaning. Comparison formulations S, which were prepared according to 199 16 036 A1, exhibited significantly poorer skin compatibility and higher skin drying-out values measured in accordance with FWT than the formulations A to J.

Moreover, the formulations A to J according to the invention exhibited a comparable very good cleaning effect in the described, standardized cleaning test in the comparison N towards a paint soiling and towards a model soiling.

The invention claimed is:
1. A composition comprising:
(a) at least 0.1% by weight of at least one polyol ester as the hydrophilic emollient with an HLB value of >10,
(b) 2 to 40% by weight of at least one surfactant selected from the group consisting of fatty alcohol ethoxylates, fatty alcohol ether sulphates, and salts of sulphated and/or sulphonated fatty acids,
(c) 30 to 90% by weight of water,
(d) 0 to 30% by weight of one or more cleaning boosters selected from the group consisting of polyols, polyethers, polyphosphates and phosphates,
(e) 0 to 30% by weight of one or more abrasives,
(f) 0 to 1.0% by weight of propoxylated fatty alcohols,
(g) optionally one or more viscosity-forming agents, and
(h) optionally further cosmetic auxiliaries, additives and/or active ingredients, the sum of components (a) to (h) being 100% by weight, wherein polyglyceryl-3 caprate is used as component (a) and PPG-11 stearyl ether is present as component (f); or wherein sucrose cocoate is used as component (a).

2. The composition according to claim 1, wherein component (b) is at least one fatty alcohol ethoxylate of general formula:

where
R =a saturated, unsaturated, branched or unbranched alkyl radical, and
n =an integer from 1 to 11.

3. The composition according to claim 1 that contains 5 to 25% by weight of one or more abrasives as component (e).

4. The composition according to claim 2 that contains 5 to 20% by weight of one or more abrasives as component (e).

5. A cleaner for removing soiling from skin or hands comprising the composition of claim 1.

6. A method for removing soiling from the skin comprising contacting soiled skin with the composition of claim 1.

7. The method of claim 6 that comprises removing soiling from hands.

8. The method of claim 6, wherein said soiling is selected from the group consisting of paint, fat, oil, a lubricant, metal dust, graphite and soot.

9. A composition comprising:
(a) 0.3 to 3% by weight of at least one polyol ester with an HLB value of ≧10, which is a sucrose ester, polyglyceryl-3 caprate or polyglyceryl-4 caprate;
(b) 5% to 10% by weight of a fatty acid ethoxylate;
(c) 45% to 75% by weight of water;

(d) more than 0 and up to 30% by weight of a cleaning booster which is a polyphosphate and/or a polyether formed from the polymerization of 3 to 20 units of ethylene glycol;
(e) 5 to 20% by weight of one or more abrasives selected from the group consisting of a polyethylene abrasive, a polyurethane abrasive, a natural kernel flour or powder, and a natural shell flour or powder;
(f) 0 to 1.0% by weight of propoxylated fatty alcohols,
(g) optionally one or more viscosity-forming agents, and
(h) optionally further cosmetic auxiliaries, additives and/or active ingredients, the sum of components (a) to (h) being 100% by weight.

10. The composition of claim 9, wherein (a) is a sucrose ester.

11. The composition of claim 9, wherein (a) is sucrose cocoate.

12. The composition of claim 9, wherein (a) is polyglyceryl-3 caprate.

13. The composition of claim 9, wherein (a) is polyglyceryl-4 caprate.

14. The composition of claim 9, wherein (a) is 0.1% to 3% by weight polyglyceryl-3 caprate, (b) is 5% to 10% by weight laureth-6, (d) is sodium tripolyphosphate, (e) is walnut shell powder, (f) is 0.1% to 0.7% by weight of PPG-11 stearyl ether, and (h) is 1% to 4% PEG-4 rapeseed amide.

15. The composition of claim 9, wherein (a) is 0.1% to 3% by weight sucrose cocoate, (b) is 5% to 10% by weight laureth-6, (d) is sodium tripolyphosphate, and (e) is walnut shell powder, and (h) is 1% to 4% PEG-4 rapeseed amide.

16. The composition of claim 1, wherein polyglyceryl-3 caprate is used as component (a) and PPG-11 stearyl ether is present as component (f).

17. The composition of claim 1, wherein (a) is 0.1% to 3% by weight polyglyceryl-3 caprate, (b) is 5% to 10% by weight laureth-6, (d) is sodium tripolyphosphate, (e) is walnut shell powder, (f) is 0.1% to 0.7% by weight of PPG-11 stearyl ether, and (h) is 1% to 4% PEG-4 rapeseed amide.

\* \* \* \* \*